(12) United States Patent
Steiner et al.

US011136604B2

(10) Patent No.: US 11,136,604 B2
(45) Date of Patent: Oct. 5, 2021

(54) (R)-SELECTIVE NITROALDOL REACTION CATALYSED BY PROTEINS OF THE CUPIN SUPERFAMILY

(71) Applicant: PATHEON AUSTRIA GMBH & CO KG, Linz (AT)

(72) Inventors: Kerstin Steiner, Graz (AT); Mandana Gruber, Graz (AT); Romana Wiedner, Graz (AT); Helmut Schwab, Graz (AT)

(73) Assignee: Patheon Austria GMBH & CO KG, Linz (AT)

( * ) Notice: Subject to any disclaimer, the term of this patent is extended or adjusted under 35 U.S.C. 154(b) by 0 days.

(21) Appl. No.: 16/535,862

(22) Filed: Aug. 8, 2019

(65) Prior Publication Data

US 2020/0040368 A1 Feb. 6, 2020

Related U.S. Application Data

(62) Division of application No. 15/317,169, filed as application No. PCT/EP2015/063195 on Jun. 12, 2015, now Pat. No. 10,421,982.

(30) Foreign Application Priority Data

Jun. 12, 2014 (EP) ..................................... 14172208

(51) Int. Cl.
*C12P 13/00* (2006.01)
*C12N 9/88* (2006.01)

(52) U.S. Cl.
CPC .............. *C12P 13/008* (2013.01); *C12N 9/88* (2013.01); *C12Y 401/02* (2013.01)

(58) Field of Classification Search
None
See application file for complete search history.

(56) References Cited

PUBLICATIONS

Dunwell JM; Biotechnol Genet Eng Rev 1998; 15:1-32.: Cupins: a new superfamily of functionally diverse proteins that include germins and plant storage proteins. 1998 (Year: 1998).*
Weidner et al., "Engineering of cupin hydroxynitrile lyases," Abstract Biotrans, ACIB (1 page).
Notice of Reasons for Rejection received in JP2016-571420 and Partial English translation of Notice of Reasons for Rejection dated Mar. 31, 2019 (22 Pages).
European Office Action for European Application No. 15728854.9 dated Feb. 13, 2019 (7 pages).
Weidner et al., "Engineering of cupin hydroxynitrile lyases," European Congress of biotechnology, Edinburgh, 13. Jul. 16, 2014, Abstract Biotrans, ACIB (1 page).
Notice of Reasons Rejection received in JP2016-571420 and Partial English translation of Reasons for Rejection dated Mar. 31, 2019 (22 Pages).
Dadashipour and Asano, "Hydroxynitrile Lyases: Insights into Biochemistry, Discovery, and Engineering," ACS Catalysis. (2011) 1121-1149.
Fuhshuku and Asano, "Synthesis of (R)-β-nitro Alcohols Catalyzed by R-Selective Hydroxynitrile Lyase from *Arabidopsis thaliana* in the Aqueous-Organic Biphasic System," J Biotechnology, vol. 153 (2011) 153-159.
Hajnal et al., "Biochemical and Structural Characterization of a Novel Bacterial Manganese-Dependent Hydroxynitrile Lyase," The FEBS Journal. vol. 280 (2013) 5815-5828.
International Search Report and Written Opinion for PCT/EP2015/063195, dated Jul. 17, 2015 (16 pages).
Lanfranchi et al., "Mini Review: Recent Developments in Hydroxynitrile Lyases for Industrial Biotechnology," Recent Patents on Biotechnology. vol. 7 (2013) 197-206.
Lyskowski et al., "Crystallization of a novel metal-containing cupin from *Acidobacterium* sp. and preliminary diffraction data analysis," Acta Crystallographica a Section F. vol. F68 (2012) 451-454.
Milner et al., "Biocatalytic Approaches to the Henry (Nitroaldol) Reaction," European Journal of Organic Chemistry. (2012) 3059-3067.
Okrob et al., "Tailoring a Stabilized Variant of Hydroxynitrile Lyase from *Arabidopsis thaliana*," ChemBioChem. vol. 13 (2012) 797-802.
Steiner et al., "Engineering of Cupin Hydroxynitrile Lyases," New Biotechnology, vol. 315 (2014) S2.
Tang et al., "Enzyme-Catalyzed Henry (Nitroaldol) Reaction," J Molecular Catalysis B: Enzymatic. vol. 63 (2010) 62-67.
Uberto and Moomaw, "Protein Similarity Networks Reveal Relationships among Sequence, Structure, and Function within the Cupin Superfamily," Plos One. vol. 8:9 (2013) 1-10.
Wang et al., "Hydrolase-Catalyzed Fast Henry Reaction of Nitroalkanes and Aldehydes in Organic Media," J Biotechnology. vol. 145 (2010) 240-243.
Ward et al., "Three Genomes from the Phylum Acidobacteria Provide Insight into the Lifestyles of these Microorganisms in Soils," Applied and Environmental Microbiology. vol. 75:7 (2009) 2046-2056.
Wiedner et al., "Discovery of a Novel (R)-Selective Bacterial Hydroxynitrile Lyase from Acidobacterium Capsulatum," Computational and Structural Biotechnology Journal. vol. 10 (2014) 58-62.
Wiedner et al., "Improving the Properties of Bacterial R-Selective Hydroxynitrile Lyases for Industrial Applications," ChemCatChem. vol. 7 (2015) 325-332.
Xia et al., "The Henry Reaction in [Bmim]PF6-Based Microemulsions Promoted by Acylase," Molecules. vol. 18 (2013) 13910-13919.
Extended European Search Report or European Patent Application No. 14172208.2, dated Nov. 24, 2014, 11 pages.

(Continued)

*Primary Examiner* — Kagnew H Gebreyesus
(74) *Attorney, Agent, or Firm* — Raymond G. Arner; Pierce Atwood LLP

(57) ABSTRACT

The present invention relates to a method for producing chiral β-nitro alcohol compounds. The invention relates in particular to an (R)-selective cupin-nitroaldolase, which enantioselectively can catalyze the Henry reaction, wherein an aldehyde or ketone compound is converted to the corresponding β-nitro alcohol compound in the presence of a nitroalkane compound and a cupin-nitroaldolase.

6 Claims, 6 Drawing Sheets
Specification includes a Sequence Listing.

(56) References Cited

PUBLICATIONS

International Preliminary Report on Patentability for International, Patent Application No. PCT/EP2015/063195 dated Dec. 15, 2016, 10 pages.

Lanfranchi et al., "Recombinant Hydroxynitrile Lyase: High Level Expression in Pichia Pastoris," ACIB GmbH—Austrian Centre of Industrial Biotechnology, 10th DocDays, Dec. 7, 2013, 1 page.

Lanfranchi et al., "Recombinant Hydroxynitrile Lyase: High Level Expression in Pichia Pastoris," ACIB GmbH—Austrian Centre of Industrial Biotechnology, 10th DocDays, Dec. 7, 2013, Abstract, 1 page.

Wiedner and Schwab, "Discovery of New and Improved Hydroxynitrile Lyases Belonging to the Cupin Superfamily," Abstract, Biotrans 2013, 2 pages.

Lanfranchi et al., "A New Hydroxynitrile Lyase from Fern: from the Plant to the Sequence," ACIB Austrian Centre of Industrial Biotechnology, Abstract Biotrans 2013, 1 page.

Lanfranchi et al., "A New Hydroxynitrile Lyase from Fern: from the Plant to the Sequence," ACIB Austrian Centre of Industrial Biotechnology, Science Days, Poster, Biotrans 2013, 1 page.

Wiedner et al., "Discovery of New and Improved Hydroxynitrile Lyases Belonging to the Cupin Superfamily," Poster, Biotrans, ACIB Austrian Centre of Industrial Biotechnology, 2013, 1 page.

Wiedner et al., "Discovery of New and Improved Hydroxynitrile Lyases Belonging to the Cupin Superfamily," Abstract Biotrans, ACIB Austrian Centre of Industrial Biotechnology, 2013, 1 page.

Wiedner et al., "Discovery of New and Improved Hydroxynitrile Lyases Belonging to the Cupin Superfamily," Poster, ACIB Science Days, 2013, 1 page.

Hajnal et al., "Biochemical and Structural Characterisation of a Novel Manganese-Dependent Hydroxynitrile Lyase from Bacteria," Poster, Enzyme Engineering 2013, 1 page.

European Office Action for European Patent Application No. 15728854.9, dated Jan. 24, 2018, 6 pages.

"Alpha/beta Hydrolase Superfamily," https://en.wikipedia.org/wiki/Alpha/beta_hydrolase_superfamily, retrieved Jul. 23, 2018, 3 pages.

"Cupin Superfamily," https://en.wikipedia.org/wiki/Cupin_superfamily, retrieved Jul. 23, 2018, 6 pages.

Gao et al., "Highly Efficient and Large-Scalable Glucoamylase-Catalyzed Henry Reactions," RSC Advances (2013) 3, 16850-16856.

Gruber-Khadjawi et al., "Hydroxynitrile Lyase—Catalyzed Enzymatic Nitroaldol (Henry) Reaction," Adv. Synth. Catal. (2007) 349, 1445-1450.

Le et al., "Henry Reaction Catalyzed by Lipase A from Aspergillus niger," Green Chemistry Letters and Reviews (2013) vol. 6, No. 4, 277-281.

López-Iglesias et al., "Use of Protease from Bacillus Licheniformis as Promiscuous Catalyst for Organic Synthesis: Applications in C—C and C—N Bond Formation Reactions," Adv. Synth. Catal. (2011) 353, 2345-2353.

Purkarthofer et al., "A Biocatalytic Henry Reaction—The Hydroxynitrile Lyase from Hevea Brasiliensis Also Catalyzes Nitroaldol Reactions," Angew Chem. Int. Ed. (2006) 45, 3454-3456.

Response filed with European Patent Office dated Nov. 29, 2017 for European Patent Application No. 15728854.9, 2 pages.

Busto et al., "Protein-Mediated Nitroaldol Addition in Aqueous Media. Catalytic Promiscuity or Unspecific Catalysis?" Organic Process Research & Development (2011) 15, 236-240.

Hussain et al., "Characterization of Two Bacterial Hydroxynitrile Lyases with High Similarity to Cupin Superfamily Proteins," Applied and Environmental Microbiology (2012) 2053-2055.

Yuryev et al., "Asymmetric Retro-Henry Reaction Catalyzed by Hydroxynitrile Lyase from Hevea Brasiliensis," ChemCatChem (2010) 2, 981-986.

Yuryev et al., "Kinetic Studies of the Asymmetric Henry Reaction Catalyzed by Hydroxynitrile Lyase from Hevea Brasiliensis," Biocatalysis and Biotransformation (2010) 28(5-6) 348-356.

* cited by examiner

FIG. 1B

```
           1.          10.         20.         30.         40.         50.         60.         70.
GthNL      MEIKRVGSQASGKGPADWFTGTVRIDPLFQAPDPALVAGASVTFEPGARTAWHTHPLGQTLIVTAGCGWA
AchNL      MQITRNGSQPSGRGPAEYFTGTVRVDPLFAAPEPARVAGASVTFEPGARTAWHTHPLGQTLIVTSGCGRV
B8ENI4     MLITRSGSQPSGKGPADWFTGAVRMDPLFSAPDPARVAGASVTFEPGARTAWHTHPLGQTLIVTAGCGWA
A5G162     MEIWRSGARDSTPGPQAYFTGSVRIDPVNTAPEPARVAAAHVTFEPGARTAWHTHPLGQTLIVTSGLGWV
C6D499     MTIRRIGTQPSGKGPFDYFTGTVRIDPLFEAPDPARVAGASVTFEPGARTAWHTHPLGQTLIVTAGSGRI
CID3E9     MKIQRVGTQPSTTGPADWFTGAVRIDGLFEPAHEPARAAGNAVTFEPGARTAWHTHPLGQTLIVTAGVGRV
A6U7V5     MEIFECGSRPSTRGPAEYFTGSVRLDPAFEAPSPARLRGATTVTFEPGARTAWHTHPLGQTLIVTAGRGLA
F8IF03     MKIVRNRERKPSAGSSATFGRVSITPVWNAEEPSRVGAAVRFEPGARTAWHTHPLGQLILEGVGWV 80.         90.         100.        110.        120.        130.
GthNL      QREGGAVEEIHPGDVVWFSPGEKHWHGAAPTTAMTHLAIQERLDGKAVDWMEHVTDEQYRR....
AchNL      QREGPVEEIRPGDVVWFTPGERHWHGASPSTAMTHIAIQEKLDGKVEWLEHVTDAEYAG....
B8ENI4     QREGGPVEEIRPGDVVWFSPGERHWHGATPTTGMTHIAIQEKLDGKTVDWLEHVSDDQYRM....
A5G162     QREGGPVEEIRPGDVVWFAPGERHWHGATPTTGMSHYAIQERLDGSAVTWLEHVTDDEYRR....
C6D499     QRWGGPIEDIFPGDVVWFPPGEKHWHGASPTTAMTHIAIQEALDGKAVEWLEKVSEDQYQG....
CID3E9     QREGGPVEEIRPGDVVWCEPGEKHWHGAAPTTALQEALDGKSVEWLEHVTDEQYQAGEAG
A6U7V5     QSWGGELREIRAGDVVWEPPGEKHWHGADTGMTHIAIQEALDGKAVDWLEHVTDEQYGGV....
F8IF03     QREGESVQEVYPGDIVWEESGERHWHGASPEHAMAHVAIQEALDGSPVDWMEHVTEAEYRRG....
```

FIG. 5:

Protein sequence of GtHNL (SEQ ID NO:1)
MEIKRVGSQASGKGPADWFTGTVRIDPLFQAPDPALVAGASVTFEPGARTAW
HTHPLGQTLIVTAGCGWAQREGGAVEEIHPGDVVWFSPGEKHWHGAAPTTA
MTHLAIQERLDGKAVDWMEHVTDEQYRR Protein sequence of GtHNL-A40H/V42T/Q110H (SEQ ID NO:2)
MEIKRVGSQASGKGPADWFTGTVRIDPLFQAPDPALVAGHSTTFEPGARTAW
HTHPLGQTLIVTAGCGWAQREGGAVEEIHPGDVVWFSPGEKHWHGAAPTTA
MTHLAIHERLDGKAVDWMEHVTDEQYRR Protein sequence of AcHNL (SEQ ID NO:3)
MQITRNGSQPSGRGPAEYFTGTVRVDPLFAAPEPARVAGASVTFEPGARTAW
HTHPLGQTLIVTSGCGRVQREGGPVEEIRPGDVVWFTPGERHWHGASPSTAM
THIAIQEKLDGKVVEWLEHVTDAEYAG Protein sequence of AcHNL-A40H/V42T/Q110H (SEQ ID NO:4)
MQITRNGSQPSGRGPAEYFTGTVRVDPLFAAPEPARVAGHSTTFEPGARTAW
HTHPLGQTLIVTSGCGRVQREGGPVEEIRPGDVVWFTPGERHWHGASPSTAM
THIAIHEKLDGKVVEWLEHVTDAEYAG Protein sequence of B8ENI4 (SEQ ID NO:5)
MLITRSGSQPSGKGPADWFTGAVRMDPLFSAPDPARVAGASVTFEPGARTAWH
THPLGQTLIVTAGCGWAQREGGPVEEIRPGDVIWFSPGEKHWHGATPTTGMTHI
AIQEKLDGKTVDWLEHVSDDQYRM Protein sequence of A5G162 (SEQ ID NO:6)
MEIWRSGARDSTPGPQAYFTGSVRIDPVNTAPEPARVAAAHVTFEPGARTAWHT
HPLGQTLIVTSGLGWVQREGGPVEEIRPGDVVWFAPGERHWHGATPTTGMSHY
AIQERLDGSAVTWLEHVTDDEYRR

FIG. 5 (Con't):

Protein sequence of C6D499 (SEQ ID NO:7)
MTIRRIGTQPSGKGPFDYFTGTVRIDPLFEAPDPARVAGASVTFEPGARTAWHTH
PLGQTLIVTAGSGRIQRWGGPIEDIFPGDVVWFPPGEKHWHGASPTTAMTHIAIQ
ERLDGKAVEWLEKVSEDQYQG Protein sequence of C1D3E9 (SEQ ID NO:8)
MKIQRVGTQPSTTGPADWFTGAVRIDGLFPAHEPARAAGNAVTFEPGARTAWH
THPLGQTLIVTAGVGRVQREGGPVEEIRPGDVVWCEPGEKHWHGAAPTTAMTHI
ALQEALDGKSVEWLEHVTDEQYQAGEAG Protein sequence of A6U7V5 (SEQ ID NO:9)
MEIFECGSRPSTRGPAEYFTGSVRLDPAFEAPSPARLRGATVTFEPGARTAWHT
HPLGQTLIVTAGRGLAQSWGGELREIRAGDVVWFPPGEKHWHGAAPDTGMTHI
AIQEALDGKAVDWLEHVTDEQYGGV Protein sequence of F8IF03 (SEQ ID NO:10)
MKIVRNRERKPSAGSSATFTGRVSITPVWNAEEPSRVGAAVVRFEPGARTAWHT
HPLGQLLIILEGVGWVQREGESVQEVYPGDIVWFESGERHWHGASPEHAMAHV
AIQEALDGSPVDWMEHVTEAEYRRG

(R)-SELECTIVE NITROALDOL REACTION CATALYSED BY PROTEINS OF THE CUPIN SUPERFAMILY

CROSS REFERENCE TO RELATED APPLICATIONS

This application is a divisional of U.S. patent application Ser. No. 14/317,169, filed Dec. 8, 2016, which is a national stage entry under 35 U.S.C. § 371 from PCT International Application No. PCT/EP2015/063195 filed Jun. 12, 2015, which claims the benefit to and priority of European Patent Application No. 14172208.2, filed Jun. 12, 2014, the subject matter of all of which is incorporated herein by reference.

FIELD OF THE INVENTION

The present invention relates to a method for producing chiral β-nitro alcohol compounds, wherein an aldehyde or ketone compound is converted to the corresponding β-nitro alcohol compound in the presence of a nitroalkane compound and a cupin-nitroaldolase. The invention relates in particular to a (R)-selective cupin-nitroaldolase which enantioselectively catalyzes the Henry reaction.

BACKGROUND ART

Biocatalytic processes have become very important to the chemical industry. Of particular importance is the use of enzymes, when the properties of biocatalysts enable either of the two enantiomers in chemical reaction with chiral or prochiral compounds to be reacted or formed preferentially.

Essential requirements for utilizing these favorable properties of enzymes are their low-cost availability in sufficient amounts, as required in industrial processes, a sufficiently high reactivity, selectivity and high stability under the realistic conditions of the industrial process.

β-nitro alcohols are precursors for β-amino alcohols, which are important chiral building blocks for the synthesis of bioactive compounds, such as ephedrine, bestatin and sphingosine, used as pharmaceutical ingredients. The nitroaldol or Henry reaction is one of the classical named reactions in organic synthesis for C—C bond formation. Due to the potential to create up to two new chiral centers it is of fundamental importance for synthetic applications to be able to perform the nitroaldol addition enantio- and stereoselectively. Although the reaction has been known for more than a century (Henry, 1895), stereospecific protocols utilizing non-enzymatic organocatalysts or chiral metal catalysts have been developed only recently. The development of these methods is impressive, but they still share a number of disadvantages, including long reaction times and sometimes extreme reaction conditions in the case of metal catalysts, or insufficient selectivities in the case of organocatalysts.

In the past decade, the first asymmetric biocatalytic nitroaldol reaction was discovered for the hydroxynitrile lyase from the tropical rubber tree *Hevea brasiliensis* (HbHNL) (Purkarthofer et al., Angew Chem Int Ed Engl. 2006 45(21):3454-6, Gruber-Khadjawi et al., Adv. Synth. Catal. 2007, 349, 1445-1450, Yuryev, R.; et al., Biocatal. Biotransform., (2010) 28, 348; Yuryev, R.; et al.; Chemcatchem, (2010) 2, 981)).

The (S)-selective MeHNL from *Manihot esculenta*, which like HbHNL belongs to the α/β-hydrolase superfamily, is also capable of catalyzing the (S)-selective nitroaldol reaction, albeit with lower activity and selectivity.

The first (R)-selective HNL, which catalyzes the (R)-selective HNL-catalyzed Henry reaction is AtHNL from *Arabidobsis thaliana* (Fuhshuku et al. J. Biotechnol. 2011, 153, 153-159), which belongs also to the α/β-hydrolase superfamily like the (S)-selective nitroaldolases.

In contrast, activity in the nitroaldol reaction has not been shown so far for the (R)-selective hydroxynitrile lyase from *Prunus amygdalus* (PaHNL), which belongs to a different protein fold.

Unfortunately, however, the enantiomeric excess of the reaction product of AtHNL decreases significantly without increase of yield during prolonged reaction times (from 2 h to 4 h) at the reported reaction conditions (Fuhshuku et al. 2011).

Asano and coworkers achieved the highest enantioselectivity for benzaldehyde and MeNO$_2$ in a biphasic system at pH 7 with 50% n-butyl acetate (30% yield and 91% ee) applying 40 mg AtHNL per mmol benzaldehyde. Yield and enantiomeric excess were further slightly improved by applying larger amounts of enzyme (100 mg per mmol of substrate). Depending on the substrate and reaction system yields up to 60% or enantiomeric excess up to 96% could be obtained applying 40 mg of AtHNL per mmol of substrate and a reaction time of 2 h. However, not coexistent under the same reaction conditions.

However, the enantiomeric excess of the reaction product of AtHNL decreases significantly without increase of yield during prolonged reaction times (from 2 h to 4 h) at the reported reaction conditions. Nitroethane was not used.

Gotor and coworkers reported the protein-mediated catalysis of the nitroaldol reaction by the carrier protein bovine serum albumin (BSA) in water, which can be categorized as organocatalysis because the observations of the scientists led to the conclusion of unspecific protein catalysis. (Busto, E.; Gotor-Fernandez, V.; Gotor, V., Org. Process Res. Dev., (2011) 15, 236). Biocatalytic nitroaldol reactions were also reported with enzymes (for a review see Milner, S. E.; et al., Eur. J. Org. Chem, (2012), 3059), such as a transglutaminase, (Tang, R. C.; et al., J. Mol. Catal. B: Enzym., (2010) 63, 62) a hydrolase, (Wang, J. L.; et al., J. Biotechnol., (2010) 145, 240) a protease, (Lopez-Iglesias, M.; et al., Adv. Synth. Catal., (2011) 353, 2345) lipases, (Le, Z.-G.; et al., Green Chem. Lett. Rev., (2013) 6, 277; Xia, W.-J.; et al., Molecules, (2013) 18, 13910), an acylase (Xia, W.-J.; et al., Molecules, (2013) 18, 13910) and a glucoamylase (Gao, N.; et al., RSC Adv., (2013) 3, 16850), but in all cases the reactions were not enantioselective or no data about enantioselectivity were provided.

Thus, so far only plant HNLs with α/β-hydrolase fold were capable of catalysing the enantioselective nitroaldol reaction.

Another approach is a chemo-enzymatic approach, in which the chemically synthesized mixture of stereoisomers is separated by enzymatic kinetic resolution, e.g. using hydrolases. However, the major drawback of kinetic resolution in general is the limitation of the yield to a maximum of 50%.

Thus, there is still the need for new nitroaldolases, which can enantioselectively catalyze the Henry reaction.

Recently, the discovery of new bacterial HNLs with cupin fold has been reported (Hajnal, I.; et al., Febs J., (2013) 280, 5815; Hussain, Z.; et al., Appl. Environ. Biotechnol., (2012) 78, 2053), however displaying only very low specific activity. One of the new enzymes, GtHNL, was characterized in detail and its structure was solved (Hajnal, I.; et al., Febs J., (2013) 280, 5815; Lyskowski, A.; et al., Acta Crystallogr. F, (2012) 68, 451). It is a small metal-dependent mono-cupin with a molecular weight of ~15 kDa, which forms a tetramer.

SUMMARY OF INVENTION

It is the objective of the present invention to provide an enhanced method for producing β-nitro alcohol compounds. The method comprises the steps of providing an aldehyde or ketone compound and converting the compound to the corresponding β-nitro alcohol compound in the presence of a nitroalkane compound and a cupin-nitroaldolase. The invention relates in particular to an (R)-selective cupin-nitroaldolase, which can enantioselectively catalyze the Henry reaction.

BRIEF DESCRIPTION OF DRAWINGS

FIG. 1B is a table showing a multi sequence alignment of SEQ ID NO: 1, NO:3 and NOS: 5-10.

FIG. 5: Protein sequence of cupin-nitroaldolases

SEQ ID NO: 1 GtHNL (*Granulicella tundricola* MP5ACTX9, Uniprot E8WYN5)

SEQ ID NO:2 Protein sequence of GtHNL triple variant (A40H, V42T, Q110H)

SEQ ID NO:3 Protein sequence of AcHNL (*Acidobacterium capsulatum* ATCC 51196; Uniprot C1F951)

SEQ ID NO:4 Protein sequence of AcHNL triple variant (A40H, V42T, Q110H)

SEQ ID NO:5 Protein sequence of a cupin 2 conserved barrel domain protein (Uniprot B8ENI4)

SEQ ID NO:6 Protein sequence of a cupin 2 conserved barrel domain protein (Uniprot A5G162)

SEQ ID NO:7 Protein sequence of a cupin 2 conserved barrel domain protein (Uniprot C6D499)

SEQ ID NO:8 Protein sequence of an uncharacterized protein (Uniprot C1D3E9)

SEQ ID NO:9 Protein sequence of a cupin 2 conserved barrel domain protein (Uniprot A6U7V5)

SEQ ID NO: 10 Protein sequence of a cupin 2 conserved barrel domain protein (Uniprot F8IF03),

DESCRIPTION OF EMBODIMENTS

In a first aspect, the invention relates to a method for producing a β-nitro alcohol compound, wherein an aldehyde or ketone compound is converted to the corresponding β-nitro alcohol compound in the presence of a nitroalkane compound and a cupin-nitroaldolase.

Figure 1A:
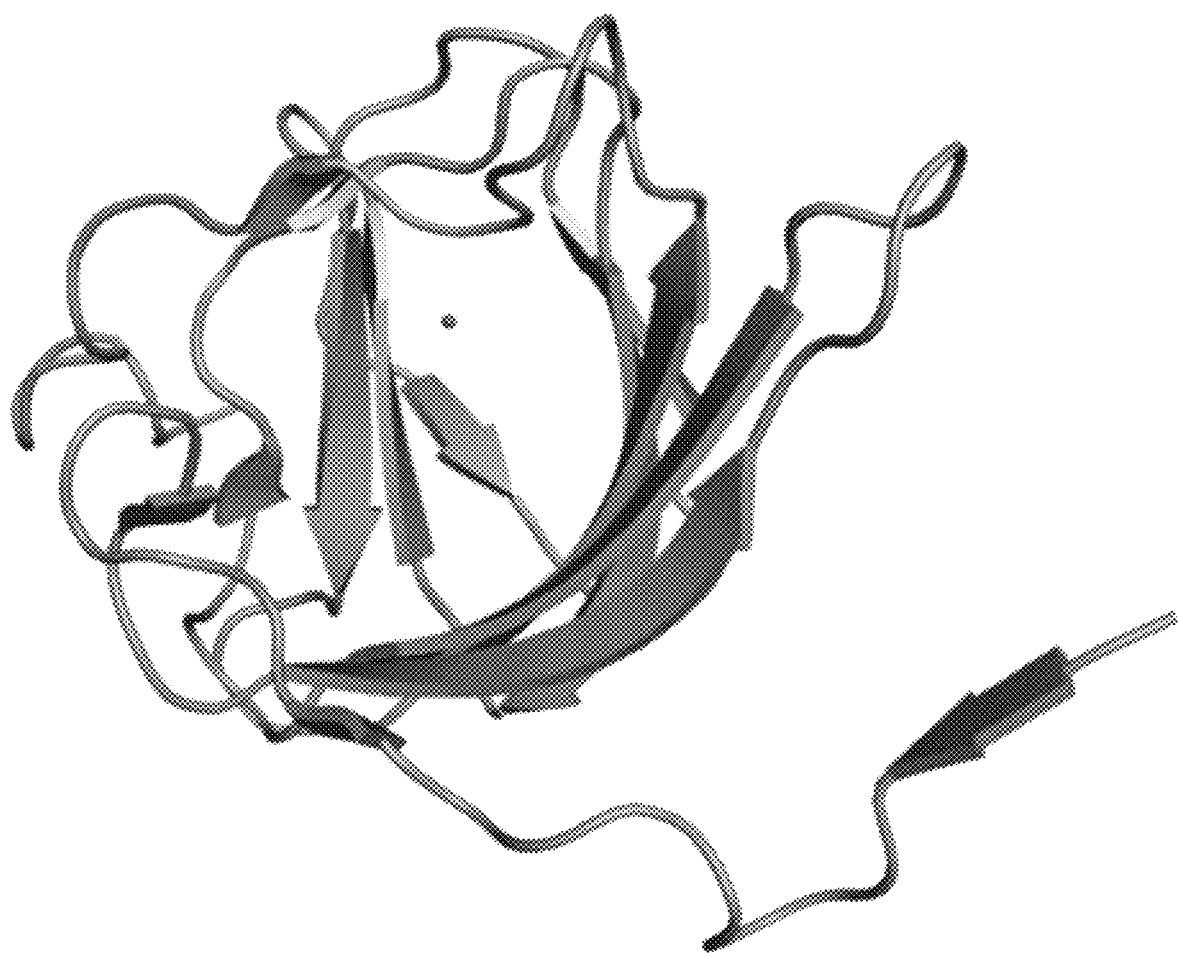
FIG. 1A: Cartoon representation of one cupin monomer of the structure of GtHNL (PDB-code: 4BIF).

In another aspect, the invention relates to a method as described above, wherein the cupin-nitroaldolase comprises a conserved barrel domain according to FIG. 1A.

In another aspect, the invention relates to a method as described above, wherein the cupin-nitroaldolase comprises a conserved barrel domain of the cupin superfamily with a PFAM accession CL0029.

In another aspect, the invention relates to a method as described above, wherein the cupin-nitroaldolase comprises a conserved barrel domain of the cupin 2 family with a PFAM accession PF07883.

In another aspect, the invention relates to a method as described above, wherein the cupin-nitroaldolase belongs to the RmlC-like cupin superfamily with a SCOP accession 51182.

In another aspect, the invention relates to a method as described above, wherein the cupin-nitroaldolase comprises a RmlC-like jelly roll fold (IPR014710) according to the InterPro protein families database.

In another aspect, the invention relates to a method as described above, wherein the cupin-nitroaldolase comprises an RmlC-like cupin domain (IPRO11051) according to the InterPro protein families database.

In another aspect, the invention relates to a method as described above, wherein the cupin-nitroaldolase comprises a cupin 2, conserved barrel domain (IPR013096) according to the InterPro protein families database.

In another aspect, the invention relates to a method as described above, wherein a compound of formula I is reacted with a compound of formula II in the presence of a cupin-nitroaldolase to yield a 3-nitro alcohol compound of formula III

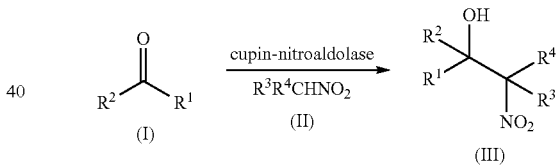

wherein
$R^1$ and $R^2$ are independently from one another H, $C_{1-20}$alkyl, $C_{2-20}$alkenyl, or $C_{2-20}$alkynyl, $C_{3-10}$cycloalkyl, $C_{4-20}$cycloalkylalkyl, $C_{6-14}$aryl, $C_{7-20}$arylalkyl, 3-14 membered heterocycloalkyl, 4-20 membered heterocycloalkylalkyl, 5-20 membered heteroaryl or 6-20 membered heteroarylalkyl, optionally substituted by one or more $R^a$;
$R^3$ and $R^4$ are independently from one another H or $C_{1-20}$alkyl, optionally substituted by one or more $R^a$; and
each $R^a$ is independently H, halogen, —$CF_3$, —$OR^b$, —$NR^bR^b$, —$(CH_2)_n COOR^b$, —$(CH_2)_n C(=O)R^b$, —$(CH_2)_n CONR^bR^b$, $C_{1-20}$alkyl, $C_{2-20}$alkenyl, or $C_{2-20}$alkynyl; and
each $R^b$ is independently H or optionally substituted $C_{1-20}$alkyl, $C_{2-20}$alkenyl, or $C_{2-20}$alkynyl; and
n is 0, 1, 2 or 3.

An alkyl group, if not stated otherwise, denotes a linear or branched $C_{1-20}$alkyl, preferably a linear or branched chain of one to twenty carbon atoms, optionally substituted. An alkyl group may be substituted by one or more $R^a$.

An alkenyl group, if not stated otherwise, denotes a partially unsaturated linear or branched $C_{2-20}$alkenyl, preferably a linear or branched chain of two to twenty carbon atoms that contains at least one double bond, optionally substituted. An alkenyl group may be substituted by one or more $R^a$.

An alkynyl group, if not stated otherwise, denotes a partially unsaturated linear or branched $C_{2-20}$alkynyl, preferably a linear or branched chain of two to twenty carbon atoms that contains at least one triple bond, optionally substituted. An alkynyl group may be substituted by one or more $R^a$.

A cycloalkyl group denotes a monocyclic non-aromatic hydrocarbon ring containing three to ten carbon atoms, preferably four to six carbon atoms, or a bicyclic non-aromatic hydrocarbon ring system containing seven to ten carbon atoms, preferably seven carbon atoms, wherein the cycloalkyl group optionally comprises one or more double or triple bonds, optionally substituted. A cycloalkyl group may be substituted by one or more $R^a$.

A heterocycloalkyl group denotes a monocyclic non-aromatic hydrocarbon ring containing three to fourteen carbon atoms, preferably four to eight carbon atoms, or a bicyclic non-aromatic hydrocarbon ring system containing seven to fourteen carbon atoms, preferably eight to ten carbon atoms, wherein in the heterocycloalkyl group one or more of the carbon atoms of the hydrocarbon ring or ring system is replaced by a group selected from the group comprising —N—, —O—, —S—, —S(O)—, —S(O)$_2$—, —Si— and —P—; wherein the heterocycloalkyl group optionally comprises one or more double bonds, optionally substituted. A heterocycloalkyl group may be substituted by one or more $R^a$.

An aryl group preferably denotes a mono-, bi- tri- or tetracyclic, preferably monocyclic aromatic hydrocarbon group having six to fourteen carbon atoms; the aryl group is preferably phenyl, optionally substituted, optionally substituted. An aryl group may be substituted by one or more $R^a$.

A heteroaryl group denotes an aromatic 5- or a 6-membered monocyclic hydrocarbon group wherein at least one of the carbon atoms is replaced by a heteroatom like O, N, and/or S, and wherein the aromatic monocyclic 5- or 6-membered cyclic hydrocarbon group is optionally fused to a further monocyclic 5- to 7-membered, preferably 5- or 6-membered, aromatic or nonaromatic hydrocarbon ring, wherein in the further monocyclic aromatic or nonaromatic hydrocarbon ring one or more, preferably one or two carbon atoms may be replaced by a heteroatom like O, N, and/or S, optionally substituted. A heteroaryl group may be substituted by one or more $R^a$.

A halogen group is chlorine, bromine, fluorine or iodine.

Optionally substituted as used herein refers to a substituent selected from the group consisting of halogen, —OH, —OCH$_3$, —CN, carbonyl and carboxyl, $C_{1-20}$alkyl, $C_{2-20}$alkenyl and $C_{2-20}$alkynyl next to substituted and unsubstituted $C_{6-14}$aryl or $C_{5-14}$heteroaryl residues.

The method can be carried out in a mono- or biphasic system or in an emulsion.

The monophasic reaction solution comprises an aqueous or an organic solvent.

Appropriate aqueous solutions are for example water, a cupin-nitroaldolase containing solution, or a buffer solution. Examples for buffer solutions are phosphate buffer, citrate buffer, acetate buffer, borate buffer, MES, HEPES, Tris buffer, or mixtures thereof. The pH of these solutions can be between pH 2 and 9, preferably from 4 to 7.

Appropriate organic solutions can be slightly water-miscible or water immiscible aliphatic or aromatic hydrocarbons, which are optionally halogenated, alcohols, ethers or esters or mixture thereof or the substrate itself. Suitable are for example, but not limited to ethyl acetate, butyl acetate, methyl tert-butyl ether, diisopropyl ether, dibutyl ether, carbon tetrachloride, benzene, toluene, cyclohexane, hexadecane, hexane, heptane, chloroform, xylene, pentanol, hexanol, octanol and dodecanol, DMF, DMSO, acetonitrile, nitromethane, nitroethane, or mixtures thereof. Also applicable are neoteric solvents, which refers to ionic liquids and supercritical fluids.

The advantages of conducting bioconversions in aqueous-organic solvent two-liquid phase systems are well known in the art. The biphasic system consists of two phases mutually not miscible, e.g. an aqueous and an organic phase.

In a further aspect, the invention relates to a method as described above, wherein the reaction is carried out in a mono- or biphasic system or in an emulsion.

In a further aspect the invention relates to a method as described above, wherein the biphasic system comprises aqueous and organic solution as described herein.

The cupin-nitroaldolases of the invention may be present here either as purified enzyme or as a whole cell suspension or contained in a cell free lysate or in immobilized form, for example on a support such as Celite®, Avicel, etc. or as cross-linked enzyme aggregate (CLEA).

The conversion moreover takes place at temperatures of from −10° C. to +50° C., preferably at 0° C. to 35° C.

The choice of applicable electrophiles ranges from aromatic to heteroaromatic and aliphatic aldehydes. Depending on the substrate and reaction systems yields up to 97.3% or enantiomeric excess >99% could be obtained by the inventive method.

In a further aspect, the invention relates to a method as described above, wherein the β-nitro alcohol compound is obtained with at least 55%, preferably with at least 60%, more preferred with at least 75% enantiomeric excess (e.e.).

In a further aspect, the invention relates to a method as described above, wherein the β-nitro alcohol compound is obtained with a conversion rate of at least 10%, preferably with at least 20%, more preferred with at least 50%.

Proteins of the cupin superfamily of proteins (PFAM: CL0029) contain a conserved beta barrel domain composed of 10 to 12 anti-parallel beta-strands (FIG. 1A). Cupa is the latin term for barrel. In the structural classification of proteins database (SCOP) they are classified as the RmlC-like cupins superfamily [51182] within the double-stranded β-helix fold. The cupin fold is found in a wide variety of enzymes, but also non-enzymatic proteins. The cupin domain can be found once, twice or more in a protein structure, either alone or in combination with other domains. Although proteins in the cupin superfamily show very low overall sequence similarity, they all contain two short but partially conserved cupin sequence motifs separated by a less conserved intermotif region that varies both in length and amino acid sequence (FIG. 1). Proteins of the cupin superfamily have a wide range of biological functions in archaea, bacteria and eukaryotes.

Cupins are structurally conserved and usually contain two conserved motifs, G-(X)$_5$—H—X—H—(X)$_{3,4}$-E-(X)$_6$-G (motif 1) and G-(X)$_5$—P—X-G-(X)$_2$—H—(X)$_3$—N (motif 2), the overall sequence identity is low among members of this superfamily. The two motifs also include the residues for metal binding. Most cupins are metal-binding proteins that bind divalent cations such as iron, zinc, manganese, copper, nickel or cadmium. The metal is usually involved in the enzymatic reaction either directly in the reaction mechanism or at least via an interaction with the substrate.

In a further aspect, the invention relates to a cupin-nitroaldolase, which is capable to catalyze the asymmetric 3-nitro alcohol reaction with a conversion rate of at least 10%, preferably of at least 20%, more preferred of at least 50%.

In a further aspect, the invention relates to a cupin-nitroaldolase, wherein the cupin-nitroaldolase comprises a conserved barrel domain according to FIG. 1A.

In a further aspect, the invention relates to a cupin-nitroaldolase, wherein the cupin-nitroaldolase comprises a conserved barrel domain of the cupin superfamily with a PFAM accession CL0029.

In a further aspect, the invention relates to a cupin-nitroaldolase, wherein the cupin-nitroaldolase comprises a conserved barrel domain of the cupin 2 family with a PFAM accession PF07883.

In a further aspect, the invention relates to a cupin-nitroaldolase, wherein the cupin-nitroaldolase belongs to the RmlC-like cupin superfamily with a SCOP accession 51182.

In another aspect, the invention relates to a cupin-nitroaldolase, wherein said cupin-nitroaldolase comprises a RmlC-like jelly roll fold (IPR014710) according to the InterPro protein families database.

In another aspect, the invention relates to a cupin-nitroaldolase, wherein the cupin-nitroaldolase comprises an RmlC-like cupin domain (IPR011051) according to the InterPro protein families database.

In another aspect, the invention relates to a cupin-nitroaldolase, wherein the cupin-nitroaldolase comprises a cupin 2, conserved barrel domain (IPR013096) according to the InterPro protein families database.

A further aspect of the invention is a cupin-nitroaldolase as described above, which is a recombinant cupin-nitroaldolase.

A further aspect of the invention is a cupin-nitroaldolase as described above, comprising at least one, specifically at least two, specifically at least three, specifically at least four, specifically at least five or more amino acids modifications.

According to the invention, the term "modification" means a deletion or substitution or insertion of at least one amino acid. Specifically, the modification is a substitution of one amino acid.

In a specific embodiment of the invention, the cupin-nitroaldolase comprises one, two or three amino acid substitutions.

According to the embodiment of the invention, any amino acid can be selected to substitute the amino acid of the wild type sequence.

The substituted amino acids are selected from arginine, lysine, histidine and threonine. Specifically, said substituted amino acids are arginine, histidine or threonine.

In a further aspect, the invention relates to a cupin-nitroaldolase as described above, wherein the amino acid sequence of the cupin-nitroaldolase is at least 85%, at least 86%, at least 87%, at least 88%, at least 89%, at least 90%, at least 91%, at least 92%, at least 93%, at least 94%, at least 95%, at least 96%, at least 97%, or at least 98% identical to the respective wild type enzyme.

In a further aspect, the invention relates to a cupin-nitroaldolase as described above, which is modified at any one of positions 40, 42 and/or 110 according to the numbering of SEQ ID NO: 1, SEQ ID NO:3 (FIG. 1B).

In a further aspect, the invention relates to a cupin-nitroaldolase as described above, which is modified at any one of positions 40, 42 and/or 110 according to the numbering of SEQ ID NO:5, SEQ ID NO:6, SEQ ID NO:7, SEQ ID NO:8, SEQ ID NO:9 or SEQ ID NO:10 (FIG. 1B).

According to the embodiment of the invention, the modification at any of positions 40, 42 and/or 110 are amino acid substitutions.

According to a further embodiment, the cupin-nitroaldolase variant of the invention contains one, two or three substitutions at any of positions 40, 42 and 110 of the conserved barrel domain.

In a further aspect, the invention relates to a cupin-nitroaldolase as described above, having the SEQ ID NO:2 (GtHNLmut) or (SEQ ID NO:4 (AcHNLmut).

According to a further embodiment, the cupin-nitroaldolase variant is A40H or A40R according to the numbering of SEQ ID NO:1, SEQ ID NO:3, or SEQ ID NO:5 to 10.

According to a further embodiment, the cupin-nitroaldolase variant is V42T or Q110H according to the numbering of SEQ ID NO: 1 or SEQ ID NO:3, or SEQ ID NO:5 to 10.

According to a further embodiment, the cupin-nitroaldolase variant is A40H V42T according to the numbering of SEQ ID NO:1 or SEQ ID NO:3, or SEQ ID NO:5 to 10.

According to a specific embodiment, the cupin-nitroaldolase variant is A40H V42T Q110H according to the numbering of SEQ ID NO: 1 or SEQ ID NO:3, or SEQ ID NO:5 to 10.

In a further aspect, the invention relates to a cupin-nitroaldolase as described above, characterized in that it comprises the amino acid sequence of the general formula:

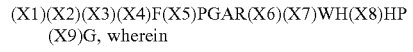
(X9)G, wherein

X1 is an A, V, L, F, Y, M, S, T, G, H, N, K or R residue, preferably it is an A, or N;
X2 is any amino acid, preferably it is S, H, A, or T;
X3 is a V, A, I, C, M, H, or T residue preferably it is a V;
X4 is any amino acid, preferably it is T or R;
X5 is any amino acid, preferably it is E;
X6 is a T, S or N residue, preferably it is T;
X7: is any amino acid, preferably it is A;
X8: is a T, S, or I residues, preferably it is T;
X9: is any amino acid preferably it is L;
and wherein at least one of positions X1, or X3 is substituted by a H, K, R or T residue.

In a further aspect, the invention relates to a cupin-nitroaldolase as described above, characterized in that it comprises the amino acid sequence of the general formula:

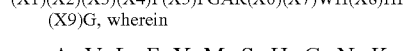
(X9)G, wherein

X1 is an A, V, L, F, Y, M, S, H, G, N, K or R residue, preferably it is an A, or N;
X2 is any amino acid, preferably it is S, H, A, or T;
X3 is a V, A, I, C, M, or T residue preferably it is V;
X4 is any amino acid, preferably it is T or R;
X5 is any amino acid, preferably it is E;
X6 is a T, S or N residue, preferably it is T;
X7: is any amino acid, preferably it is A;
X8: is a T, S, or I residues, preferably it is T;
X9: is any amino acid preferably it is L;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X9)G, wherein

X1 is an A, V, L, F, Y, M, S, T, G, N, K or R residue, preferably it is an A, or N;
X2 is any amino acid, preferably it is S, H, A, or T;

X3 is a V, A, I, C, M, or H residue preferably it is V;
X4 is any amino acid, preferably it is T or R;
X5 is any amino acid, preferably it is E;
X6 is a T, S or N residue, preferably it is T;
X7: is any amino acid, preferably it is A;
X8: is a T, S, or I residues, preferably it is T;
X9: is any amino acid preferably it is L;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)F(X5)PGAR(X6)(X7)WH(X8)HP(X9)G, wherein

X1 is an A, V, L, F, Y, M, S, G, N, K or R residue, preferably it is A, or N;
X2 is any amino acid, preferably it is S, H, A, or T;
X3 is a V, A, I, C, or M residue preferably it is V;
X4 is any amino acid, preferably it is T or R;
X5 is any amino acid, preferably it is E;
X6 is a T, S or N residue, preferably it is T;
X7: is any amino acid, preferably it is A;
X8: is a T, S, or I residues, preferably it is T;
X9: is any amino acid preferably it is L;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)FEPGARTAWHTHPLG, wherein

X1 is an A, V, L, F, Y, M, S, T, G, H, K, N or R residue, preferably it is an A, or N;
X2 is any amino acid, preferably it is S, H, A, or T;
X3 is a V, A, I, C, M, H, or T residue preferably it is V;
X4 is any amino acid, preferably it is T or R;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)FEPGARTAWHTHPLG, wherein

X1 is an A, V, L, F, Y, M, S, T, G, H, or N residue, preferably it is an A, or N;
X2 is any amino acid preferably it is S, H, A, or T;
X3 is a V, A, I, C, M, H, or T residue preferably it is V;
X4 is any amino acid preferably it is T or R;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)FEPGARTAWHTHPLG, wherein

X1 is an A, V, L, F, Y, M, S, T, G, H, K, N or R residue, preferably it is an A, or N;
X2 is any amino acid, preferably it is S, H, A, or T;
X3 is V;
X4 is any amino acid, preferably it is T or R;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)FEPGARTAWHTHPLG, wherein

X1 is an A, V, L, F, Y, M, S, G, N, K or R residue, preferably it is A, or N;
X2 is any amino acid, preferably it is S, H, A, or T;
X3 is a V, A, I, C, or M residue preferably it is V;
X4 is any amino acid, preferably it is T or R;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)FEPGARTAWHTHPLG, wherein

X1 is an A, or N residue, preferably it is A;
X2 is any amino acid, preferably it is S, H, A, or T;
X3 is a V, A, I, C, or M residue preferably it is V;
X4 is any amino acid, preferably it is T or R;
and wherein at least one of positions X1, or X3 is substituted by a H, K, R or T residue.

In a further aspect, the invention relates to a cupin-nitroaldolase as described above, characterized in that it comprises the amino acid sequence of the general formula:

(X1)(X2)(X3)(X4)FEPGARTAWHTHPLG, wherein

X1 is an A, or N residue, preferably it is A;
X2 is any amino acid preferably it is S, H, A, or T;
X3 is V;
X4 is any amino acid preferably it is T or R;
and wherein at least one of positions X1, or X3 is substituted by a H, K, R or T residue.

In a further aspect, the invention relates to a cupin-nitroaldolase having one or more of following mutations A40H, A40R, V42T and/or Q110H according to the numbering of SEQ ID NO: 1 or 3 or SEQ ID NO:5 to 10.

In a further aspect, the invention relates to an isolated polynucleic acid molecule encoding a cupin-nitroaldolase as described above.

In a further aspect of the present invention an isolated polynucleic acid molecule is provided encoding a cupin-nitroaldolase as described above. The polynucleic acid may be DNA or RNA. Thereby the modifications which lead to encoding the inventive cupin-nitroaldolase as described above are carried out on DNA or RNA level. This isolated polynucleic acid molecule is suitable for the production of inventive cupin-nitroaldolase as described above on a large scale.

In a further aspect, the invention relates to a vector comprising an isolated DNA molecule as described above.

The vector comprises all regulatory elements necessary for efficient transfection as well as efficient expression of proteins. Such vectors are well known in the art and any suitable vector can be selected for this purpose.

A further aspect of the present invention relates to a recombinant non-human cell which is transfected with an inventive vector as described above. Transfection of cells and cultivation of recombinant cells can be performed as well known in the art. Such a recombinant cell as well as any therefrom descendant cell comprises the vector. Thereby a cell line is provided which expresses the inventive cupin-nitroaldolase protein either continuously or upon activation depending on the vector.

In a further aspect, the invention relates to a culture obtained by culturing the recombinant cell as described above.

The recombinant cells may be cultured in the presence of a metal ion, preferably in the presence of iron or manganese.

In a further aspect, the invention relates to a cupin-nitroaldolase recovered from the culture as described above.

Specifically, the protein can be isolated by disrupting the cells and recovering the protein from the supernatant.

In a further aspect, the invention relates to a method for producing a cupin-nitroaldolase, comprising recovering the cupin-nitroaldolase from the culture as described above. Said isolation or purification from the cell culture can be performed by methods known in the art. Specifically, affinity chromatography, anion-exchange chromatography and size exclusion chromatography can be used to isolate said protein.

In a further aspect, the invention relates to a cupin-nitroaldolase produced as described above, which is incubated with a solution of metal salts in buffer, for example $FeCl_2$, $MnCl_2$, $CoCl_2$, $NiCl_2$, $CuCl_2$ or $ZnCl_2$ by methods know to the art.

In a further aspect, the invention relates to a cupin-nitroaldolase produced as described above, which in which the metal is exchanged in vitro to manganese, iron, nickel, cobalt, copper or zinc by methods known to the art.

EXAMPLES

The Examples which follow are set forth to aid in the understanding of the invention but are not intended to, and should not be construed to limit the scope of the invention in any way. The Examples do not include detailed descriptions of conventional methods, e.g., cloning, transfection, and basic aspects of methods for overexpressing proteins in microbial host cells. Such methods are well known to those of ordinary skill in the art.

Example 1. Protein Production

The gene (gene ID: NC_012483) encoding a hypothetical protein from *Acidobacterium capsulatum* ATCC 51196 (Uniprot C1F951, Ward et al., Appl. Environ. Microbiol (2009) 75, 2046) was ordered codon-optimized for *E. coli* (GeneArt, Life Technologies, Carlsbad, Calif., USA) (named AcHNL in the following). The coding region was flanked by the NdeI and HindIII restriction sites, which were used to clone the gene into the expression vector pET26b(+) (Novagen, Merck KGaA, Darmstadt, Germany).

The sequence encoding AciX9_0562 (gene ID: 322434201) corresponding to GtHNL from *Granulicella tundricula*, which is codon-optimized for *E. coli*, was previously cloned into the expression vector pET26b(+) (Hajnal et al., FEBS J. 2013 280(22):5815-28). GtHNL was used as template for semi-rational protein design, in more detail, site-saturation mutagenesis. The mutations A40H, V42T and Q110H resulted in improved variants. The best amino acid exchanges at position A40, V42 and Q110 were combined by site-directed mutagenesis. The same amino acid exchanges at position A40, V42 and Q110 were subsequently also introduced in the sequence of AcHNL by site-directed mutagenesis.

*E. coli* BL21-Gold(DE3) was used as expression host (Stratagene, La Jolla, Calif., USA). The cells were grown in LB (lysogeny broth, Lennox) medium (Carl Roth GmbH, Karlsruhe, Germany) supplemented with kanamycin sulphate (40 mg/L final concentration). Expression of recombinant protein was initiated by addition of 0.5 mM IPTG (isopropyl 3-D-1-thiogalactopyranoside) to OD600~0.8 cultures, and cultivation was continued at 25° C. for 20 h. All enzymes were grown with manganese present in the expression medium. Routinely, 100 μM of $MnCl_2$ was added concomitantly with the induction. The cells were harvested, resuspended in cold buffer (50 mM potassium phosphate buffer pH 6.0) and disrupted by sonification (Branson Sonifier S-250, set to 80% duty cycle, and output control 7) two times for 3 min, cooled on ice. The cell lysate was centrifuged for an hour at 50,000 g to remove unbroken cells and insoluble material. The cell free lysate was filtered through a 0.45 m syringe filter and if necessary concentrated to the desired concentration using Vivaspin 20 Centrifugal Filter Units (10,000 Da molecular-weight cut-off; Sartorius). The lysate was aliquoted and frozen until further use. Protein expression was monitored by standard SDS-PAGE. AcHNL and GtHNL as well as the variants of GtHNL and AcHNL containing the amino acid substitutions A40H, A40R, V42T and Q110H were expressed in high yield as soluble protein in *E. coli* BL21-Gold(DE3) reaching yields of >50% of total soluble protein.

The purification procedure was adapted from a protocol published for GtHNL applying anion-exchange chromatography and size exclusion chromatography (Hajnal et al., 2013). In short, the cells were lysed by sonication in Buffer A (50 mM Bis-Tris/HCl, pH 6.8 or 6.9, 50 mM NaCl), and the cleared lysates were loaded on a QSepharose anion-exchange column (HiTrap™ Q FF 5 mL, GE Healthcare, Uppsala, Sweden). The proteins were eluted with 10% buffer B (50 mM Bis-Tris/HCl, pH 6.6, 1 M NaCl). Size exclusion chromatography was performed on a Superdex 75 HiLoad 16/600 column (GE Healthcare, Uppsala, Sweden) pre-equilibrated with 50 mM NaPi, pH 7.0, 100 mM NaCl. Fractions containing the proteins of interest were pooled, and the buffer was exchanged to 50 mM KPi, pH 6.0 on PD-10 columns (GE Healthcare, Uppsala, Sweden). Protein concentrations of cell free lysates were routinely determined using the Bradford assay (Biorad, Hercules, Calif., USA). Concentrations of purified proteins were determined with a Nanodrop spectrophotometer (model 2000c, Peqlab, Erlangen, Germany) at 280 nm applying an extinction coefficient calculated based on the amino acid sequence using Protparam. The protein was stored at −80° C. or −20° C. until further use. The successful incorporation was confirmed by inductively coupled plasma/optical emission spectroscopy (ICP-OES).

Example 2. Nitroaldol Reaction in a Biphasic System

The ability of these enzymes to catalyze the synthesis of 3-nitroalcohols was examined using a two-phase system consisting of benzaldehyde and nitromethane dissolved in MTBE as organic phase and an aqueous phase comprising cell free lysate or purified enzymes in phosphate buffer at pH 6.

Organic solvent (500 μL MTBE) containing internal standard (0.2% 1,3,5-triisopropylbenzene, IS), benzaldehyde (20 μmol, BA) and nitromethane (1 mmol, NM) was mixed with 500 μL of 50 mM potassium phosphate buffer, pH 6, containing either cell free lysate (~0.5-3 mg of total protein containing ~50% cupin nitroaldolase) or purified enzyme (~0.3-1.5 mg). As negative controls either cell free lysate without enzyme, AcHNL expressed in the absence of $MnCl_2$, or just buffer with and without $MnCl_2$ were used. As positive control AtHNL (2-3 mg), which was ordered as synthetic gene and cloned into pET28a(+)-vector, expressed and purified as described by Asano's group (Fuhshuku et al., 2011), was used. Note that due to stability issues of AtHNL at lower pH, it was applied at pH 6.5. The mixture was incubated at 30° C. and 1200 rpm for 2-24 hours in an Eppendorf Thermomixer device. The reaction was stopped by centrifugation at 13,000 rpm for 5 minutes. Fifty μL of the organic phase were diluted with 450 μL of the HPLC solvent mixture and analyzed by chiral HPLC.

Figure 2:
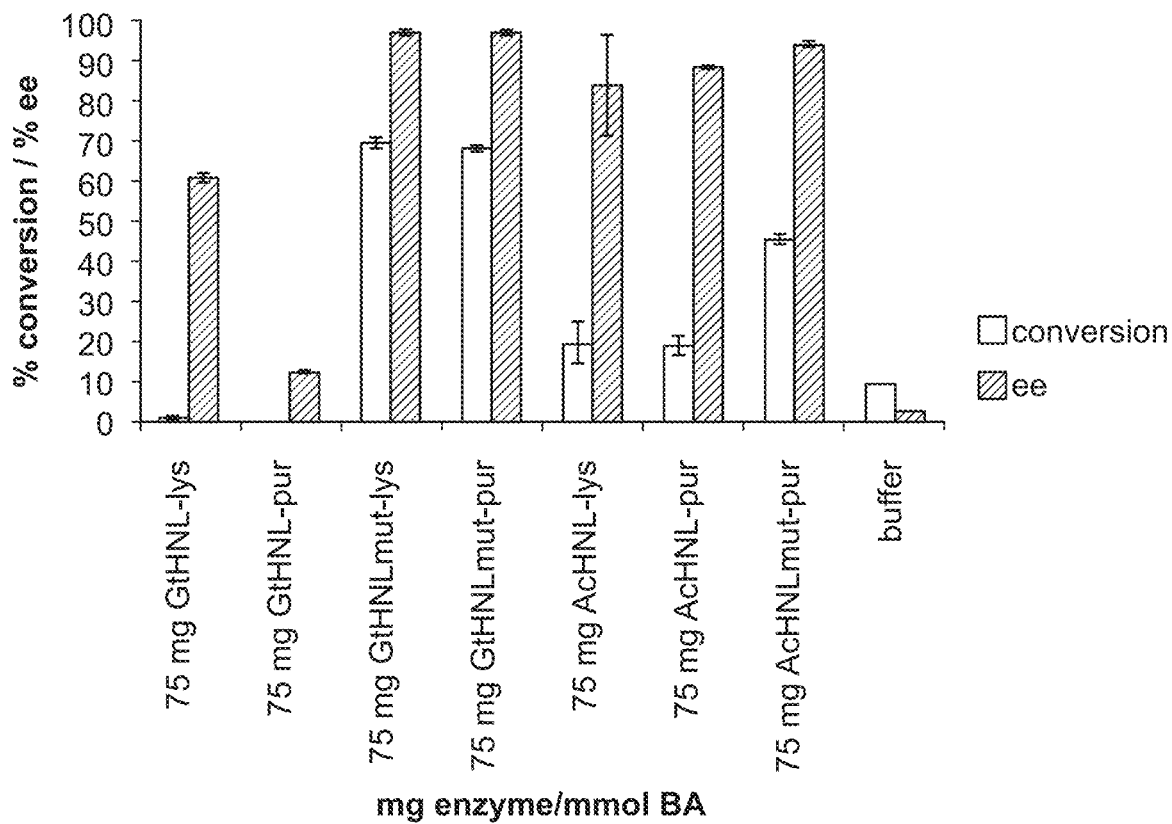
FIG. 2: Nitroaldol reaction of AcHNL and GtHNL and the triple variants of GtHNL (GtHNL-A40H/V42T/Q110H, short: GtHNLmut) and AcHNL (AcHNL-A40H/V42T/Q110H, short: AcHNLmut) with benzaldehyde (20 tmol) and nitromethane (1 mmol) in a biphasic system with 50% TBME. Cleared lysate (the amount of enzyme/mmol BA refers to the enzyme itself assuming that ~50% of total lysate protein are HNL) or purified enzyme was used. Conversion and ee values measured after 6 h reaction time.

The results of the first cupin-nitroaldolase catalyzed Henry reaction with benzaldehyde and nitromethane are shown in FIG. 2 and Table 1.

TABLE 1

Conversion and ee values related to FIG. 2.

| mg enzyme/mmol BA | conversion [%] | ee [%] |
|---|---|---|
| 75 mg GtHNL-A40H/V42T/Q110H-lysate | 69.9 | 97.5 |
| 75 mg GtHNL-A40H/V42T/Q110H-purified | 68.5 | 97.3 |
| 75 mg AcHNL-WT-lysate | 19.5 | 84.1 |
| 75 mg AcHNL-WT-purified | 19.2 | 88.4 |
| 75 mg AcHNL-A40H/V42T/Q110H-purified | 45.5 | 94.2 |
| buffer | 9.8 | 2.3 | n.d.: not determined due to too low conversion

AcHNL showed a conversion of 19% and an ee of 88% after 6 h of incubation. GtHNL-A40H/V42T/Q110H, achieved almost 70% conversion and 97% ee. No difference was observed if cleared lysates or purified enzymes were applied. Thus, the purified enzymes are stable under the applied reaction conditions, but on the other hand do not need to be purified to obtain good to excellent ee values. All negative controls, AcHNL, which was expressed in the absence of $MnCl_2$, as well as $MnCl_2$ applied in buffer or in E. coli lysate without enzyme, were inactive. Thus, both the cupin protein and manganese are necessary in combination for nitroaldol activity.

Figure 3:
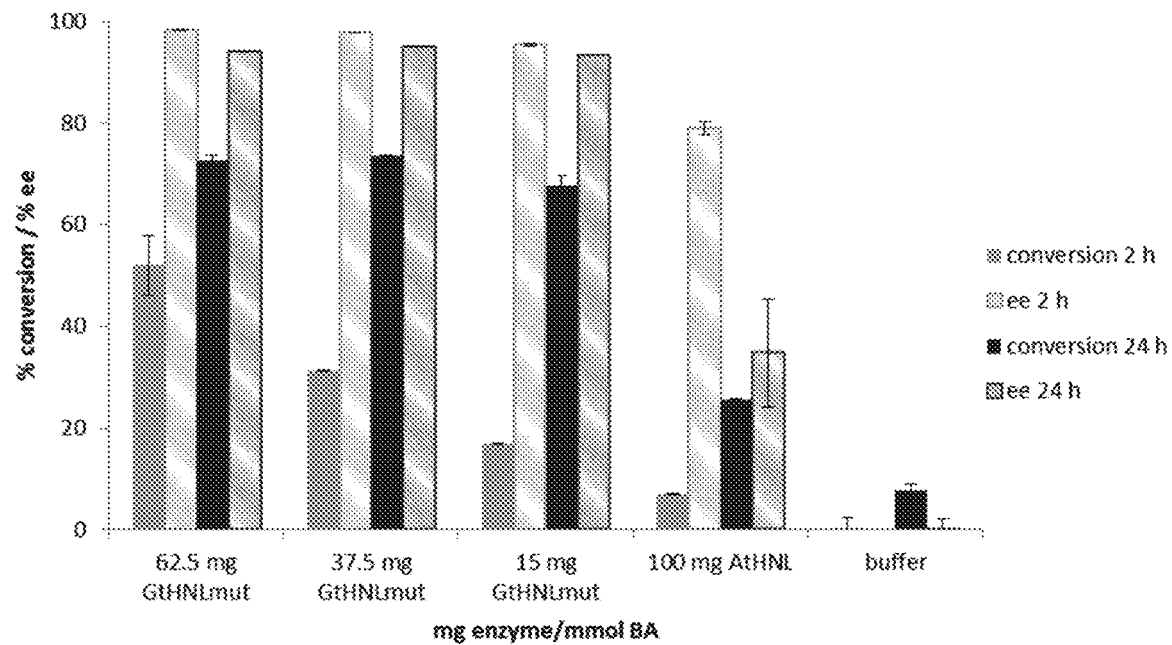
FIG. 3: Nitroaldol reaction of the triple variant GtHNL-A40H/V42T/Q110H (short: GtHNLmut) with benzaldehyde (20 tmol) and nitromethane (1 mmol) in a biphasic system with 50% TBME, and different protein to substrate ratios. AtHNL was used as reference. Conversion and ee values were measured after 2 h and 24 h reaction time.

To investigate further if also lower amounts of enzyme can achieve good conversions, if the ee can be further improved applying shorter reaction times, and if the ee is stable during longer incubation times the reactions with GtHNL-A40H/V42T/Q110H were repeated (FIG. 3 and Table 2).

TABLE 2

Conversion and ee values related to FIG. 3.

| Reaction time | 2 h | | 24 h | |
|---|---|---|---|---|
| mg enzyme/mmol BA | conv. [%] | ee [%] | conv. [%] | ee [%] |
| 62.5 mg GtHNL-A40H/V42T/Q110H | 52.0 | 98.4 | 72.6 | 94.1 |
| 37.5 mg GtHNL-A40H/V42T/Q110H | 31.4 | 97.8 | 73.7 | 95.0 |
| 15 mg GtHNL-A40H/V42T/Q110H | 17.0 | 95.5 | 67.7 | 93.4 |
| 100 mg AtHNL | 7.1 | 78.9 | 25.8 | 34.8 |
| buffer | 0.6 | n.d. | 7.8 | 0.2 | n.d.: not determined due to too low conversion

Compared to values reported in literature for AtHNL (Fuhshuku et al., 2011) and also determined by us, the above mentioned newly discovered GtHNL triple variant is more active than AtHNL, and it shows a higher enantioselectivity.

Importantly, in contrast to AtHNL higher yields can be achieved with GtHNL-A40H/V42T/Q110H by longer incubation times losing almost no enantioselectivity.

Single variants of AcHNL and GtHNL were tested for their ability to catalyze the nitroaldol reaction.

TABLE 3

Conversion and ee values.

| enzyme | mg enzyme/mmol BA | time [h] | Conversion % | ee (R) % |
|---|---|---|---|---|
| AcHNL lysate | 12.5 | 4 | 2.5 ± 0.3 | 57.9 ± 0.1 |
| | | 24 | 17.8 ± 0.2 | 55.5 ± 0.3 |
| | 50 | 24 | 38.5 ± 0.7 | 77.3 ± 0.3 |
| AcHNL purified | 25 | 2 | 4.2 ± 0.2 | 78.8 ± 1.2 |
| | | 4 | 7.7 ± 0.1 | 80.3 ± 0.1 |
| | | 24 | 37.5 ± 1.8 | 78.9 ± 0.0 |
| AcHNL-A40H lysate | 12.5 | 4 | 33.3 ± 0.4 | 96.7 ± 0.1 |
| | | 24 | 73.4 ± 0.0 | 95.3 ± 0.1 |
| AcHNL-A40H purified | 25 | 2 | 62.9 ± 0.6 | 99.3 ± 0.0 |
| | | 4 | 72.7 ± 0.9 | 99.3 ± 0.0 |
| | | 24 | 74.0 ± 0.1 | 97.0 ± 0.1 |
| AcHNL-A40R lysate | 12.5 | 4 | 50.2 ± 0.5 | 97.4 ± 0.0 |
| AcHNL-A40R purified | 25 | 2 | 57.3 ± 0.9 | 98.5 ± 0.1 |
| | | 4 | 67.7 ± 0.3 | 98.3 ± 0.0 |
| | | 24 | 73.3 ± 0.2 | 96.0 ± 0.1 |
| AcHNL-V42T lysate | 50 | 24 | 48.9 ± 0.0 | 84.7 ± 0.1 |
| AcHNL-Q110H lysate | 50 | 24 | 17.2 ± 0.1 | 47.3 ± 0.1 |
| AcHNL-A40H/V42T/Q110H lysate | 12.5 | 4 | 12.0 ± 0.4 | 89.5 ± 0.4 |
| | | 24 | 50.4 ± 0.7 | 88.5 ± 0.3 |
| AcHNL-A40H/V42T/Q110H purified | 25 | 2 | 11.4 ± 0.0 | 94.6 ± 0.0 |
| | | 4 | 21.2 ± 0.3 | 93.9 ± 0.7 |
| | | 24 | 66.3 ± 0.1 | 93.2 ± 0.1 |
| GtHNL-A40H lysate | 12.5 | 4 | 14.1 ± 0.4 | 90.8 ± 1.1 |
| | | 24 | 53.8 ± 0.6 | 89.7 ± 0.0 |
| GtHNL-A40H purified | 25 | 2 | 22.7 ± 0.1 | 96.3 ± 0.1 |
| | | 4 | 38.3 ± 0.5 | 96.7 ± 0.1 |
| | | 24 | 74.2 ± 0.0 | 95.5 ± 0.0 |
| GtHNL-A40R lysate | 12.5 | 4 | 50.1 ± 0.1 | 97.2 ± 0.0 |
| | | 24 | 74.0 ± 0.0 | 94.3 ± 0.1 |
| GtHNL-A40R purified | 25 | 2 | 55.9 ± 0.1 | 98.1 ± 0.0 |
| | | 4 | 70.5 ± 0.1 | 97.9 ± 0.1 |
| | | 24 | 75.2 ± 0.4 | 94.0 ± 0.2 |
| GtHNL-V42T lysate | 50 | 24 | 31.2 ± 0.1 | 74.1 ± 0.6 |
| GtHNL-Q110H lysate | 50 | 24 | 27.9 ± 1.1 | 68.1 ± 0.1 |
| GtHNL-A40H/V42T lysate | 12.5 | 4 | 8.3 ± 0.1 | 85.0 ± 0.5 |
| | | 24 | 39.9 ± 0.7 | 83.7 ± 0.4 |
| GtHNL-A40H/V42T/Q110H lysate | 12.5 | 4 | 11.8 ± 0.1 | 88.4 ± 0.2 |
| | | 24 | 50.1 ± 0.2 | 88.0 ± 0.2 |
| GtHNL-A40H/V42T/Q110H purified | 25 | 2 | 17.9 ± 0.8 | 95.3 ± 0.2 |
| | | 4 | 30.6 ± 0.1 | 95.8 ± 0.1 |
| | | 24 | 72.8 ± 0.4 | 94.5 ± 0.0 |

Example 3. Nitroethane Addition to Benzaldehyde

Purified AcHNL, AcHNL-A40H, AcHNL-A40R, AcHNL-A40H/V42T/Q11 OH, GtHNL-A40R and GtHNL-A40H/V42T/Q110H were tested for their ability to use nitroethane instead of nitromethane in the nitroaldol reaction. The reactions were performed as described in Example 2, with the difference that 1 mmol nitroethane instead of nitromethane was used.

Figure 4:
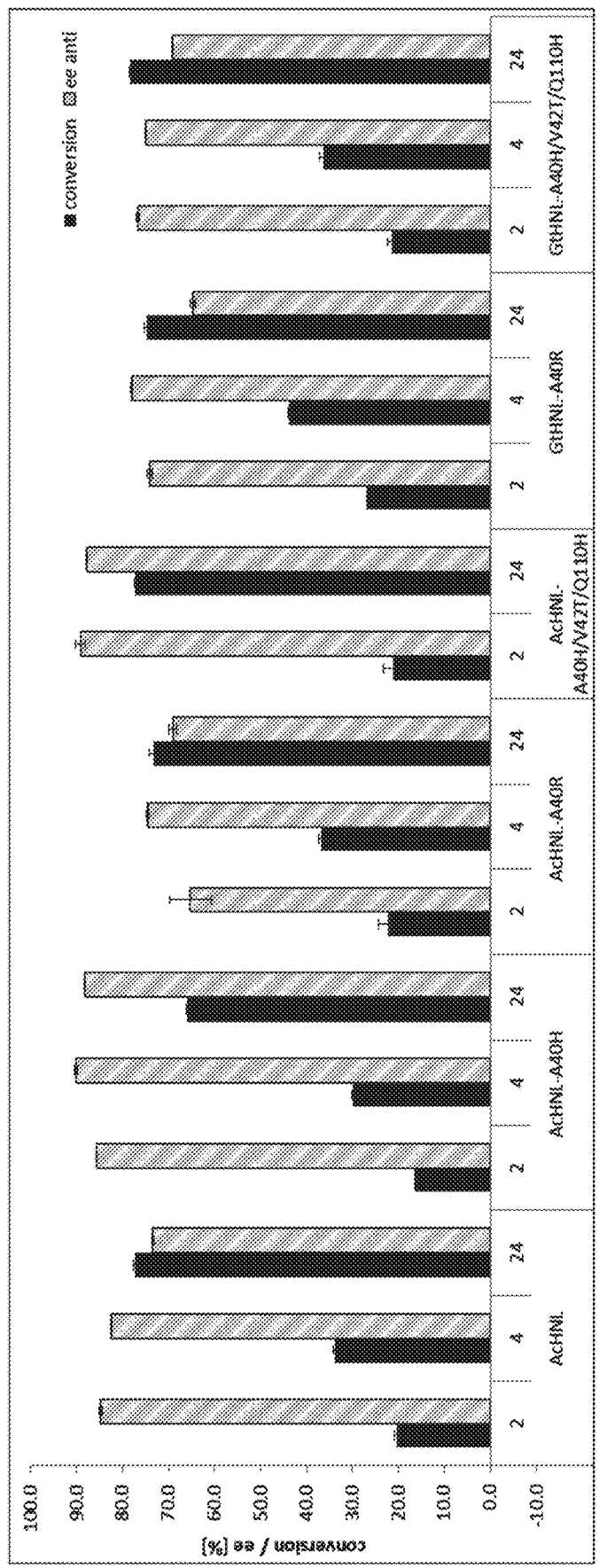
FIG. 4: Nitroaldol reaction of several cupin-nitroaldolases with benzaldehyde (20 mol) and nitroethane (1 mmol) in a biphasic system with 50% TBME. Conversion and ee values were measured after 2 h, 4 h and 24 h reaction time.

The results of the first cupin-nitroaldolase catalyzed Henry reaction using purified enzyme with benzaldehyde and nitroethane are shown in FIG. 4 and Table 4.

TABLE 4

Conversion and ee values related to FIG. 4.

| purified enzyme | mg enzyme/mmol BA | time [h] | conversion [%] | ee (R, anti) [%] |
|---|---|---|---|---|
| AcHNL | 500 | 2 | 20.3 ± 0.5 | 84.8 ± 0.3 |
| | | 4 | 33.9 ± 0.3 | 82.5 ± 0.1 |
| | | 24 | 77.4 ± 0.2 | 73.4 ± 0.2 |

TABLE 4-continued

Conversion and ee values related to FIG. 4.

| purified enzyme | mg enzyme/ mmol BA | time [h] | conversion [%] | ee (R, anti) [%] |
|---|---|---|---|---|
| AcHNL-A40H | 125 | 2 | 16.4 ± 0.0 | 85.7 ± 0.2 |
|  |  | 4 | 30.0 ± 0.1 | 90.1 ± 0.3 |
|  |  | 24 | 66.0 ± 0.0 | 88.3 ± 0.1 |
| AcHNL-A40R | 125 | 2 | 22.3 ± 1.9 | 65.2 ± 4.5 |
|  |  | 4 | 36.7 ± 0.6 | 74.5 ± 0.2 |
|  |  | 24 | 73.1 ± 1.0 | 69.0 ± 0.8 |
| AcHNL-A40H/V42T/Q110H | 500 | 2 | 21.3 ± 2.1 | 89.1 ± 1.0 |
|  |  | 24 | 77.2 ± 0.1 | 87.7 ± 0.1 |
| GtHNL-A40R | 125 | 2 | 26.9 ± 0.0 | 74.1 ± 0.6 |
|  |  | 4 | 43.8 ± 0.2 | 78.0 ± 0.2 |
|  |  | 24 | 74.8 ± 0.4 | 64.7 ± 0.5 |
| GtHNL-A40H/V42T/Q110H | 500 | 2 | 21.5 ± 1.0 | 76.7 ± 0.4 |
|  |  | 4 | 36.4 ± 0.7 | 74.9 ± 0.1 |
|  |  | 24 | 78.4 ± 0.2 | 69.1 ± 0.0 |

The addition of nitroethane to benzaldehyde produces two new stereocenters simultaneously and a diastereomeric mixture of 2-nitro-1-phenylpropanol was obtained. After 2 h of reaction time, the anti/syn ratio of AcHNL was 2:1 and the enantiomeric excess of the anti isomer was 85%. Thus, the product mixture contains about 60% of the expected main product (1R,2S)-2-nitro-1-phenylpropanol. With the single variant, AcHNL-A40H, the proportion of (1R,2S)-2-nitro-1-phenylpropanol was further increased to 70%.

Example 4. Nitromethane Addition to Various Aldehydes

The reactions were performed as described in Example 2, with the modification that instead of benzaldehyde, either 2-Cl-benzaldehyde, hexanal or cyclohexanecarboxaldehyde were used.

TABLE 5

Conversion and ee values.

R—CHO + CH$_3$NO$_2$ $\xrightarrow{\text{HNL}}$ R-CH(OH)-CH$_2$-NO$_2$ (R)

1 → 2

| R | Purified protein | Conversion [%] | ee (R) [%] |
|---|---|---|---|
| 2-ClC$_6$H$_4$ | GtHNL-A40R | 97.3 ± 0.0 | 23.2 ± 0.1 |
|  | GtHNL-A40H/V42T/Q110H | 95.0 ± 0.4 | 56.3 ± 0.2 |
|  | AcHNL-A40H | 89.0 ± 0.9 | 83.1 ± 0.5 |
|  | AcHNL-A40R | 95.3 ± 0.2 | 80.0 ± 0.2 |
|  | AcHNL-A40H/V42T/Q110H | 90.6 ± 1.3 | 54.8 ± 0.2 |
| cyclohexyl | GtHNL-A40R | 31.1 ± 0.8 | 47.0 ± 1.5 |
|  | GtHNL-A40H/V42T/Q110H | 86.3 ± 0.6 | 96.9 ± 0.1 |
|  | AcHNL-A40H | 48.2 ± 0.1 | 87.6 ± 0.5 |
|  | AcHNL-A40R | 39.7 ± 1.8 | 77.8 ± 1.4 |
|  | AcHNL-A40H/V42T/Q110H | 80.7 ± 1.3 | 95.7 ± 0.3 |
| CH$_3$(CH$_2$)$_4$ | GtHNL-A40R | 92.0 ± 0.3 | 98.0 ± 0.0 |
|  | GtHNL-A40H/V42T/Q110H | 95.0 ± 0.0 | 99.3 ± 0.0 |
|  | AcHNL-A40H | 88.8 ± 0.2 | 98.9 ± 0.0 |
|  | AcHNL-A40R | 87.9 ± 0.2 | 98.2 ± 0.1 |
|  | AcHNL-A40H/V42T/Q110H | 93.7 ± 0.2 | 99.2 ± 0.0 |

Reaction conditions: aldehyde (20 mM) and nitromethane (1 M) in a biphasic system consisting of TBME and 50 mM KPi, pH 6.0, 1:1, reaction volume 1 mL, 30° C., 1200 rpm, 24 h. Purified enzyme (2.5 mg) was used.

Example 5. Metal-Dependence of Nitroaldol Reaction

For the removal of metal ions from GtHNL-A40H/V42T/Q110H, the purified protein (as described in Example 1) was dialysed against 20 mM 2,4-pyridinedicarboxylic acid monohydrate (PDCA) in 100 mM sodium acetate and 150 mM NaCl, pH 5.5, for 50 h, and subsequently dialysed against 20 mM Tris/HCl, pH 7.5, for 20 h. The resulting apoprotein was incubated with a 10-fold molar excess of either FeCl$_2$, MnCl$_2$, CoCl$_2$, NiCl$_2$ or ZnCl$_2$ for 2.5 h at room temperature. Unbound metal was removed and the buffer was exchanged to 50 mM KPi, pH 6.0, using PD-10 columns. Metal analysis was performed by ICP-OES.

The reactions were performed as described in Example 2.

TABLE 6

Conversion and ee values.

|  | mg enzyme/ mmol BA | time [h] | Conversion % | ee % |
|---|---|---|---|---|
| GtHNL-A40H/V42T/Q110H(Mn)[a] | 25 | 4 | 28.5 ± 1.9 | 95.2 ± 0.5 |
|  | 100 | 24 | 75.8 ± 0.0 | 95.1 ± 0.2 |
| GtHNL-A40H/V42T/Q110H_Apo[b] | 25 | 4 | 4.2 ± 0.4 | 60.7 ± 0.8 |
|  | 100 | 24 | 36.1 ± 0.4 | 77.0 ± 0.3 |
| GtHNL-A40H/V42T/Q110H_Mn[c] | 25 | 4 | 33.7 ± 0.6 | 96.2 ± 0.3 |
|  | 100 | 24 | 75.7 ± 0.1 | 94.7 ± 0.2 |
| GtHNL-A40H/V42T/Q110H_Fe[c] | 25 | 4 | 41.3 ± 1.1 | 97.2 ± 0.2 |
|  | 100 | 24 | 75.7 ± 0.1 | 95.7 ± 0.1 |
| GtHNL-A40H/V42T/Q110H_Zn[c] | 25 | 4 | 19.0 ± 0.7 | 91.4 ± 0.0 |
|  | 100 | 24 | 75.7 ± 0.2 | 95.2 ± 0.0 |
| GtHNL-A40H/V42T/Q110H_Co[c] | 25 | 4 | 44.8 ± 0.5 | 97.3 ± 0.0 |
|  | 100 | 24 | 75.7 ± 0.0 | 95.7 ± 0.2 |
| GtHNL-A40H/V42T/Q110H_Ni[c] | 25 | 4 | 23.8 ± 1.9 | 93.4 ± 0.4 |
|  | 100 | 24 | 75.6 ± 0.1 | 95.1 ± 0.0 |

[a]GtHNL-A40H/V42T/Q110H was expressed in the presence of MnCl$_2$ in the expression medium.
[b]Bound metal was removed by the chelator 2,4-pyridinedicarboxylic acid. Traces of manganese were detected by ICP-OES.
[c]Apoprotein was incubated with the respective metal salts.

Example 6. Other Cupin-HNLs with Nitroaldol Activity

Several other cupins with sequence identities to SEQ ID NO: 1 and 3 between 58 and 84% (Wiedner, R.; et al., Comp. Struct. Biotechnol. J., (2014), 10, 58) were tested for their ability to catalyze the nitroaldol reaction. Protein expression and preparation of cell-free lysates were performed as described in Example 1.

TABLE 7

Cupin-HNLs with high to moderate sequence identity (seq id) to SEQ ID NO: 1 and 3.

| SEQ ID NO | Uniprot Accession number | Organism | % seq id to SEQ ID NO: 1 | % seq id to SEQ ID NO: 3 | Sequencing date |
|---|---|---|---|---|---|
| 5 | B8ENI4 | Methylocella silvestris BL2 | 84 | 81 | 2008[1] |
| 6 | A5G162 | Acidiphilium cryptum JF-5 | 74 | 76 | 2007 |
| 7 | C6D499 | Paenibacillus sp. JDR-2 | 78 | 79 | 2009 |
| 8 | C1D3E9 | Deinococcus deserti (strain VCD115/DSM 17065/LMG 22923) | 77 | 77 | 2009[2] |
| 9 | A6U7V5 | Sinorhizobium medicae WSM419 | 73 | 73 | 2007[3] |

TABLE 7-continued

Cupin-HNLs with high to moderate sequence identity (seq id) to SEQ ID NO: 1 and 3.

| SEQ ID NO | Uniprot Accession number | Organism | % seq id to SEQ ID NO: 1 | % seq id to SEQ ID NO: 3 | Sequencing date |
|---|---|---|---|---|---|
| 10 | F8IF03 | *Alicyclobacillus acidocaldarius* subsp. *acidocaldarius* Tc-4-1 | 58 | 60 | 2011[4] |

[1] Chen Y, Crombie A, Rahman MT, Dedysh SN, Liesack W et al. (2010) J Bacteriol 192: 3840-3841.
[2] de Groot A, Dulermo R, Ortet P, Blanchard L, Guerin P et al. (2009) JPLoS Genet 5. Available: http://dx.plos.org/10.1371/journal.pgen.1000434.
[3] Reeve W, Chain P, O'Hara G, Ardley J, Nandesena K et al. (2010) Genomic Sci 2: 77-86.
[4] Chen Y, He Y, Zhang B, Yang J, Li W et al. (2011) J Bacteriol 193: 5602-5603.

The reactions were performed as described in Example 2.

TABLE 8

Conversion and ee values

| Enzyme | mg enzyme/ mmol BA | Time [h] | Conversion [%] | ee [%] |
|---|---|---|---|---|
| AcHNL | 500 | 24 | 86.7 ± 1.0 | 81.0 ± 0.5 |
| B8ENI4 | | | 73.3 ± 1.0 | 69.1 ± 0.1 |
| A5G162 | | | 75.3 ± 2.8 | 55.0 ± 0.5 |
| C6D499 | | | 82.0 ± 0.2 | 71.5 ± 0.4 |
| C1D3E9 | | | 82.9 ± 0.2 | 85.2 ± 0.1 |
| A6U7V5 | | | 69.2 ± 4.1 | 60.3 ± 0.2 |
| F8IF03 | | | 72.4 ± 1.5 | 75.5 ± 0.4 |

Example 7. Nitroaldol Reaction in an Aqueous System

The ability of cupin-nitroaldolases to catalyze the synthesis of β-nitroalcohols was examined using a one-phase aqueous system consisting of 5 µmol benzaldehyde, 0.3 mmol nitromethane, and 0.375 mg of total lysate protein (containing ~50% cupin-nitroaldolase) or 0.5 mg of purified protein in 500 µL of 50 mM potassium phosphate buffer at pH 6. After incubation at 30° C. and 1200 rpm for 1 h, the reaction was stopped by extraction with 500 µL MTBE containing 0.2% internal standard (1,3,5-triisopropylbenzene, IS). Fifty µL of the organic phase were diluted with 450 µL of the HPLC solvent mixture and analyzed by chiral HPLC.

Results of the first cupin-nitroaldolase catalyzed Henry reaction in an aqueous system with benzaldehyde and nitromethane are shown in Table 9.

TABLE 9

Conversion and ee values.

| | mg enzyme/ mmol BA | time [h] | Conversion % | ee % |
|---|---|---|---|---|
| GtHNL-A40H/V42T/Q110H lysate | 37.5 | 1 | 71.1 | 94.9 |
| GtHNL-A40H/V42T/Q110H purified | 200 | 1 | 74.8 | 82.2 |

The invention claimed is:

1. A cupin-nitroaldolase variant protein characterized in that it comprises the amino acid sequence of the general formula:

(X1)(X2)(X3)(X4)F(X5)PGAR(X6)(X7)WH(X8)HP(X9)G, wherein

X1 is an A, V, L, F, Y, M, S, T, G, H, N, K, or R residue;
X2 is any amino acid;
X3 is a V, A, I, C, M, H, or T residue;
X4 is any amino acid;
X5 is any amino acid;
X6 is a T, S or N residue;
X7: is any amino acid;
X8: is a T, S, or I residues;
X9: is any amino acid;
and wherein at least one of positions X1, or X3 is substituted by a H, K, R or T residue.

2. The cupin-nitroaldolase variant protein according to claim 1, wherein in the general characterized in that it comprises the amino acid sequence of the general formula (X1)(X2)(X3)(X4)F(X5)PGAR(X6)(X7)WH(X8)HP(X9)G, X1 is an A or N residue;
X2 is an S, H, A or T residue;
X3 is a V residue;
X4 is a T or R residue;
X5 is an E residue;
X6 is a T residue;
X7: is an A residue;
X8: is a T residue;
X9: is an L residue;
and wherein at least one of positions X1, or X3 is substituted by a H, K, R or T residue.

3. The cupin-nitroaldolase variant protein according to claim 1, wherein the cupin-nitroaldolase is at least 85% identical to the respective wild type enzyme.

4. The cupin-nitroaldolase variant protein according to claim 2, wherein the cupin-nitroaldolase is at least 85% identical to the respective wild type enzyme.

5. The cupin-nitroaldolase variant protein according to claim 1 having one or more of the following mutations: A4OH, A4OR, V42T and/or Q110H according to the amino acid numbering of SEQ ID NO: 1 or 3 or SEQ ID NO: 5 to 10.

6. The cupin-nitroaldolase variant protein according to claim 1 having the amino acid sequence of SEQ ID NO: 2 or 4.

* * * * *

SEQUENCE LISTING

```
<160> NUMBER OF SEQ ID NOS: 10

<210> SEQ ID NO 1
<211> LENGTH: 131
<212> TYPE: PRT
<213> ORGANISM: Granulicella tundricola

<400> SEQUENCE: 1

Met Glu Ile Lys Arg Val Gly Ser Gln Ala Ser Gly Lys Gly Pro Ala
1               5                   10                  15

Asp Trp Phe Thr Gly Thr Val Arg Ile Asp Pro Leu Phe Gln Ala Pro
            20                  25                  30

Asp Pro Ala Leu Val Ala Gly Ala Ser Val Thr Phe Glu Pro Gly Ala
        35                  40                  45

Arg Thr Ala Trp His Thr His Pro Leu Gly Gln Thr Leu Ile Val Thr
    50                  55                  60

Ala Gly Cys Gly Trp Ala Gln Arg Glu Gly Ala Val Glu Glu Ile
65                  70                  75                  80

His Pro Gly Asp Val Val Trp Phe Ser Pro Gly Glu Lys His Trp His
                85                  90                  95

Gly Ala Ala Pro Thr Thr Ala Met Thr His Leu Ala Ile Gln Glu Arg
            100                 105                 110

Leu Asp Gly Lys Ala Val Asp Trp Met Glu His Val Thr Asp Glu Gln
        115                 120                 125

Tyr Arg Arg
    130
```

-continued

<210> SEQ ID NO 2
<211> LENGTH: 131
<212> TYPE: PRT
<213> ORGANISM: Artificial Sequence
<220> FEATURE:
<223> OTHER INFORMATION: GtHNL-A40H/V42T/Q110H

<400> SEQUENCE: 2

```
Met Glu Ile Lys Arg Val Gly Ser Gln Ala Ser Gly Lys Gly Pro Ala
1               5                   10                  15

Asp Trp Phe Thr Gly Thr Val Arg Ile Asp Pro Leu Phe Gln Ala Pro
            20                  25                  30

Asp Pro Ala Leu Val Ala Gly His Ser Thr Thr Phe Glu Pro Gly Ala
        35                  40                  45

Arg Thr Ala Trp His Thr His Pro Leu Gly Gln Thr Leu Ile Val Thr
    50                  55                  60

Ala Gly Cys Gly Trp Ala Gln Arg Glu Gly Gly Ala Val Glu Glu Ile
65                  70                  75                  80

His Pro Gly Asp Val Val Trp Phe Ser Pro Gly Glu Lys His Trp His
                85                  90                  95

Gly Ala Ala Pro Thr Thr Ala Met Thr His Leu Ala Ile His Glu Arg
            100                 105                 110

Leu Asp Gly Lys Ala Val Asp Trp Met Glu His Val Thr Asp Glu Gln
        115                 120                 125

Tyr Arg Arg
    130
```

<210> SEQ ID NO 3
<211> LENGTH: 131
<212> TYPE: PRT
<213> ORGANISM: Acidobacterium capsulatum

<400> SEQUENCE: 3

```
Met Gln Ile Thr Arg Asn Gly Ser Gln Pro Ser Gly Arg Gly Pro Ala
1               5                   10                  15

Glu Tyr Phe Thr Gly Thr Val Arg Val Asp Pro Leu Phe Ala Ala Pro
            20                  25                  30

Glu Pro Ala Arg Val Ala Gly Ala Ser Val Thr Phe Glu Pro Gly Ala
        35                  40                  45

Arg Thr Ala Trp His Thr His Pro Leu Gly Gln Thr Leu Ile Val Thr
    50                  55                  60

Ser Gly Cys Gly Arg Val Gln Arg Glu Gly Gly Pro Val Glu Glu Ile
65                  70                  75                  80

Arg Pro Gly Asp Val Val Trp Phe Thr Pro Gly Glu Arg His Trp His
                85                  90                  95

Gly Ala Ser Pro Ser Thr Ala Met Thr His Ile Ala Ile Gln Glu Lys
            100                 105                 110

Leu Asp Gly Lys Val Val Glu Trp Leu Glu His Val Thr Asp Ala Glu
        115                 120                 125

Tyr Ala Gly
    130
```

<210> SEQ ID NO 4
<211> LENGTH: 131
<212> TYPE: PRT
<213> ORGANISM: Artificial Sequence
<220> FEATURE:
<223> OTHER INFORMATION: AcHNL-A40H/V42T/Q110H

<400> SEQUENCE: 4

```
Met Gln Ile Thr Arg Asn Gly Ser Gln Pro Ser Gly Arg Gly Pro Ala
1               5                   10                  15

Glu Tyr Phe Thr Gly Thr Val Arg Val Asp Pro Leu Phe Ala Ala Pro
            20                  25                  30

Glu Pro Ala Arg Val Ala Gly His Ser Thr Thr Phe Glu Pro Gly Ala
        35                  40                  45

Arg Thr Ala Trp His Thr His Pro Leu Gly Gln Thr Leu Ile Val Thr
    50                  55                  60

Ser Gly Cys Gly Arg Val Gln Arg Glu Gly Gly Pro Val Glu Glu Ile
65                  70                  75                  80

Arg Pro Gly Asp Val Val Trp Phe Thr Pro Gly Glu Arg His Trp His
                85                  90                  95

Gly Ala Ser Pro Ser Thr Ala Met Thr His Ile Ala Ile His Glu Lys
            100                 105                 110

Leu Asp Gly Lys Val Val Glu Trp Leu Glu His Val Thr Asp Ala Glu
            115                 120                 125

Tyr Ala Gly
        130
```

<210> SEQ ID NO 5
<211> LENGTH: 131
<212> TYPE: PRT
<213> ORGANISM: Methylocella silvestris

<400> SEQUENCE: 5

```
Met Leu Ile Thr Arg Ser Gly Ser Gln Pro Ser Gly Lys Gly Pro Ala
1               5                   10                  15

Asp Trp Phe Thr Gly Ala Val Arg Met Asp Pro Leu Phe Ser Ala Pro
            20                  25                  30

Asp Pro Ala Arg Val Ala Gly Ala Ser Val Thr Phe Glu Pro Gly Ala
        35                  40                  45

Arg Thr Ala Trp His Thr His Pro Leu Gly Gln Thr Leu Ile Val Thr
    50                  55                  60

Ala Gly Cys Gly Trp Ala Gln Arg Glu Gly Gly Pro Val Glu Glu Ile
65                  70                  75                  80

Arg Pro Gly Asp Val Ile Trp Phe Ser Pro Gly Glu Lys His Trp His
                85                  90                  95

Gly Ala Thr Pro Thr Thr Gly Met Thr His Ile Ala Ile Gln Glu Lys
            100                 105                 110

Leu Asp Gly Lys Thr Val Asp Trp Leu Glu His Val Ser Asp Asp Gln
            115                 120                 125

Tyr Arg Met
        130
```

<210> SEQ ID NO 6
<211> LENGTH: 131
<212> TYPE: PRT
<213> ORGANISM: Acidiphilium cryptum

<400> SEQUENCE: 6

```
Met Glu Ile Trp Arg Ser Gly Ala Arg Asp Ser Thr Pro Gly Pro Gln
1               5                   10                  15

Ala Tyr Phe Thr Gly Ser Val Arg Ile Asp Pro Val Asn Thr Ala Pro
            20                  25                  30

Glu Pro Ala Arg Val Ala Ala Ala His Val Thr Phe Glu Pro Gly Ala
```

```
                35                  40                  45
Arg Thr Ala Trp His Thr His Pro Leu Gly Gln Thr Leu Ile Val Thr
 50                  55                  60

Ser Gly Leu Gly Trp Val Gln Arg Glu Gly Gly Pro Val Glu Glu Ile
 65                  70                  75                  80

Arg Pro Gly Asp Val Val Trp Phe Ala Pro Gly Glu Arg His Trp His
                 85                  90                  95

Gly Ala Thr Pro Thr Thr Gly Met Ser His Tyr Ala Ile Gln Glu Arg
                100                 105                 110

Leu Asp Gly Ser Ala Val Thr Trp Leu Glu His Val Thr Asp Asp Glu
            115                 120                 125

Tyr Arg Arg
        130

<210> SEQ ID NO 7
<211> LENGTH: 131
<212> TYPE: PRT
<213> ORGANISM: Paenibacillus sp.

<400> SEQUENCE: 7

Met Thr Ile Arg Arg Ile Gly Thr Gln Pro Ser Gly Lys Gly Pro Phe
 1               5                  10                  15

Asp Tyr Phe Thr Gly Thr Val Arg Ile Asp Pro Leu Phe Glu Ala Pro
                20                  25                  30

Asp Pro Ala Arg Val Ala Gly Ala Ser Val Thr Phe Glu Pro Gly Ala
            35                  40                  45

Arg Thr Ala Trp His Thr His Pro Leu Gly Gln Thr Leu Ile Val Thr
 50                  55                  60

Ala Gly Ser Gly Arg Ile Gln Arg Trp Gly Gly Pro Ile Glu Asp Ile
 65                  70                  75                  80

Phe Pro Gly Asp Val Val Trp Phe Pro Pro Gly Glu Lys His Trp His
                 85                  90                  95

Gly Ala Ser Pro Thr Thr Ala Met Thr His Ile Ala Ile Gln Glu Arg
                100                 105                 110

Leu Asp Gly Lys Ala Val Glu Trp Leu Glu Lys Val Ser Glu Asp Gln
            115                 120                 125

Tyr Gln Gly
    130

<210> SEQ ID NO 8
<211> LENGTH: 135
<212> TYPE: PRT
<213> ORGANISM: Deinococcus sp.

<400> SEQUENCE: 8

Met Lys Ile Gln Arg Val Gly Thr Gln Pro Ser Thr Thr Gly Pro Ala
 1               5                  10                  15

Asp Trp Phe Thr Gly Ala Val Arg Ile Asp Gly Leu Phe Pro Ala His
                20                  25                  30

Glu Pro Ala Arg Ala Ala Gly Asn Ala Val Thr Phe Glu Pro Gly Ala
            35                  40                  45

Arg Thr Ala Trp His Thr His Pro Leu Gly Gln Thr Leu Ile Val Thr
 50                  55                  60

Ala Gly Val Gly Arg Val Gln Arg Glu Gly Gly Pro Val Glu Glu Ile
 65                  70                  75                  80

Arg Pro Gly Asp Val Val Trp Cys Glu Pro Gly Glu Lys His Trp His
```

```
            85                  90                  95

Gly Ala Ala Pro Thr Thr Ala Met Thr His Ile Ala Leu Gln Glu Ala
            100                 105                 110

Leu Asp Gly Lys Ser Val Glu Trp Leu Glu His Val Thr Asp Glu Gln
            115                 120                 125

Tyr Gln Ala Gly Glu Ala Gly
            130                 135

<210> SEQ ID NO 9
<211> LENGTH: 132
<212> TYPE: PRT
<213> ORGANISM: Sinorhizobium medicae

<400> SEQUENCE: 9

Met Glu Ile Phe Glu Cys Gly Ser Arg Pro Ser Thr Arg Gly Pro Ala
1               5                   10                  15

Glu Tyr Phe Thr Gly Ser Val Arg Leu Asp Pro Ala Phe Glu Ala Pro
            20                  25                  30

Ser Pro Ala Arg Leu Arg Gly Ala Thr Val Thr Phe Glu Pro Gly Ala
            35                  40                  45

Arg Thr Ala Trp His Thr His Pro Leu Gly Gln Thr Leu Ile Val Thr
        50                  55                  60

Ala Gly Arg Gly Leu Ala Gln Ser Trp Gly Glu Leu Arg Glu Ile
65                  70                  75                  80

Arg Ala Gly Asp Val Val Trp Phe Pro Pro Gly Glu Lys His Trp His
                85                  90                  95

Gly Ala Ala Pro Asp Thr Gly Met Thr His Ile Ala Ile Gln Glu Ala
            100                 105                 110

Leu Asp Gly Lys Ala Val Asp Trp Leu Glu His Val Thr Asp Glu Gln
            115                 120                 125

Tyr Gly Gly Val
            130

<210> SEQ ID NO 10
<211> LENGTH: 132
<212> TYPE: PRT
<213> ORGANISM: Alicyclobacillus acidocaldarius

<400> SEQUENCE: 10

Met Lys Ile Val Arg Asn Arg Glu Arg Lys Pro Ser Ala Gly Ser Ser
1               5                   10                  15

Ala Thr Phe Thr Gly Arg Val Ser Ile Thr Pro Val Trp Asn Ala Glu
            20                  25                  30

Glu Pro Ser Arg Val Gly Ala Ala Val Val Arg Phe Glu Pro Gly Ala
            35                  40                  45

Arg Thr Ala Trp His Thr His Pro Leu Gly Gln Leu Leu Ile Ile Leu
        50                  55                  60

Glu Gly Val Gly Trp Val Gln Arg Gly Glu Ser Val Gln Glu Val
65                  70                  75                  80

Tyr Pro Gly Asp Ile Val Trp Phe Glu Ser Gly Glu Arg His Trp His
                85                  90                  95

Gly Ala Ser Pro Glu His Ala Met Ala His Val Ala Ile Gln Glu Ala
            100                 105                 110
```

```
Leu Asp Gly Ser Pro Val Asp Trp Met Glu His Val Thr Glu Ala Glu
        115             120             125
Tyr Arg Arg Gly
    130
```